(12) United States Patent
Gotschy et al.

(10) Patent No.: US 8,605,279 B2
(45) Date of Patent: *Dec. 10, 2013

(54) MICRO CUVETTE ASSEMBLY AND METHOD FOR EXAMINING BIOLOGICAL SAMPLES

(75) Inventors: Walter Gotschy, Adnet (AT); Josef Grassl, Schönau am Königsee (DE); Fritz Payr, Salzburg (AT); Markus Schürf, BergenBernhaupten (DE)

(73) Assignee: Tecan Trading AG, Mannedorf (CH)

( * ) Notice: Subject to any disclaimer, the term of this patent is extended or adjusted under 35 U.S.C. 154(b) by 635 days.

This patent is subject to a terminal disclaimer.

(21) Appl. No.: 12/240,099

(22) Filed: Sep. 29, 2008

(65) Prior Publication Data

US 2009/0086198 A1    Apr. 2, 2009

(30) Foreign Application Priority Data

Oct. 1, 2007    (CH) ..................................... 1515/07

(51) Int. Cl.
*G01N 21/01*    (2006.01)

(52) U.S. Cl.
USPC ............................ 356/246; 356/440; 422/68.1

(58) Field of Classification Search
USPC ............................ 356/246; 422/503, 551–554
See application file for complete search history.

(56) References Cited

U.S. PATENT DOCUMENTS 2,561,339 A * 7/1951 Chediak ........................ 422/552
3,819,277 A * 6/1974 Berthelot et al. ............. 356/435

(Continued)

FOREIGN PATENT DOCUMENTS

EP    0075605    4/1983
EP    0834729    4/1998

(Continued)

OTHER PUBLICATIONS

ND-1000 Spectrophotometer V3.3 User's Manual; NanoDrop Technologies, Inc.; Rev. Mar. 2006.

(Continued)

*Primary Examiner* — Kara E Geisel
*Assistant Examiner* — Rebecca C Bryant
(74) *Attorney, Agent, or Firm* — Notaro, Michalos & Zaccaria P.C.

(57) ABSTRACT

Relates to a micro cuvette assembly (1), comprising a first partial plate (2) with one or more first cuvette surfaces (3) and a second partial plate (4) which is arrangeable relative to the first partial plate and has at least one or more second cuvette surfaces (5) which, in an active position of the micro cuvette assembly (1), are arranged in register plane-parallel to the first cuvette surfaces (3) and spaced apart by a distance (6), thus forming, in the active position of the micro cuvette assembly (1), one or more micro cuvettes (7) in which a liquid volume (8) applied previously to one of the cuvette surfaces (3,5) is held between these two cuvette surfaces (3,5). The micro cuvette assembly (1) according to the present invention is characterized in that each of the first cuvette surfaces (3) of the first partial plate (2) is formed individually and completely in each case by a surface of a transparent body (10) which is accomplished as a free beam optical element and arranged in each case in an opening (9) penetrating the first partial plate (2). Also disclosed is the use of this micro cuvette assembly (1) in the carrying-out of a method for examining biological samples.

20 Claims, 3 Drawing Sheets

(56) References Cited

U.S. PATENT DOCUMENTS

| | | | |
|---|---|---|---|
| 4,466,740 A * | 8/1984 | Kano et al. | 356/246 |
| 4,722,598 A | 2/1988 | Ford | |
| 4,946,952 A * | 8/1990 | Kiefer | 536/25.41 |
| 5,255,976 A * | 10/1993 | Connelly | 374/31 |
| 5,290,521 A * | 3/1994 | DeStefano, Jr. | 422/99 |
| 6,432,719 B1 * | 8/2002 | Vann et al. | 436/180 |
| 6,486,947 B2 * | 11/2002 | Modlin et al. | 356/246 |
| 6,565,813 B1 | 5/2003 | Garyantes | |
| 6,628,382 B2 | 9/2003 | Robertson | |
| 6,809,826 B2 * | 10/2004 | Robertson | 356/440 |
| 6,953,695 B1 * | 10/2005 | Langowski | 436/172 |
| 7,138,270 B2 * | 11/2006 | Papkovsky et al. | 435/288.4 |
| 7,514,045 B2 * | 4/2009 | Corcoran et al. | 422/100 |
| 7,547,424 B2 * | 6/2009 | Haab et al. | 422/307 |
| 7,595,874 B1 * | 9/2009 | Pelekhaty et al. | 356/318 |
| 2003/0180191 A1 * | 9/2003 | Suzuki et al. | 422/102 |
| 2008/0106742 A1 | 5/2008 | Sahiri et al. | |
| 2009/0073435 A1 | 3/2009 | Tsukuda | |

FOREIGN PATENT DOCUMENTS

| | | |
|---|---|---|
| FR | 2363098 | 9/1977 |
| WO | WO 99/39829 | 8/1999 |
| WO | WO 9939829 A1 | 8/1999 |
| WO | WO02/087763 | 11/2002 |
| WO | WO 02/087763 A1 | 11/2002 |
| WO | WO 2005/114146 A1 | 12/2005 |

OTHER PUBLICATIONS

Society for Biomolecular Sciences for Microplates—Footprint Dimensions; Secretariat Society for Biomolecular Screening; American National Standards Institute; Jan. 25, 2006.

* cited by examiner

MICRO CUVETTE ASSEMBLY AND METHOD FOR EXAMINING BIOLOGICAL SAMPLES

This patent application claims priority of the Swiss patent application No. CH 01515/07 filed on Oct. 1, 2007.

According to the preamble of independent claim 1, the invention relates to a micro cuvette assembly comprising a first partial plate with one or more first cuvette surfaces and a second partial plate which is arrangeable relative to the first partial plate and has at least one or more second cuvette surfaces. These second cuvette surfaces are, in an active position of the micro cuvette assembly, arranged in register plane-parallel to the first cuvette surfaces and spaced apart by a distance. Thus, in the active position of the micro cuvette assembly, one or more micro cuvettes are formed in which a liquid volume applied previously to one of the cuvette surfaces is held between these two cuvette surfaces. Each of these partial plates preferably has in each case a uniform array of a plurality of cuvette surfaces, wherein it is especially preferred for these uniform arrangements of a plurality of cuvette surfaces to be accomplished as a linear array with 8 cuvette surfaces or as an integral multiple of such linear arrays arranged parallel to one another. The invention additionally relates to a corresponding method.

Microplates for providing a large number of "virtual wells" are known in the art. For example, U.S. Pat. No. 6,565,813 B1 discloses microplates of this type having a format similar to the format of a standard microplate. In this case, there is provided on two glass partial plates drawn close together a respective array of hydrophilic domains of opposing register. The hydrophilic domains are typically surrounded by a hydrophobic Teflon® (DuPont) field which is applied, for example, by means of screen printing. The liquid volumes are thus braced between the two hydrophilic domains of a "virtual well" and held in place. Alternative embodiments with domains which are hydrophilised by oxidation for the samples are also described. These microplates, which are used for example for high throughput screening, are preferably used to produce test mixtures with reagents of very low volumes of from 100 nl to 10 µl, the results of which can be evaluated, for example, by means of fluorometry. Nevertheless, these microplates are not suitable for absorption measurements, because the path lengths in the "virtual wells" are not defined sufficiently precisely.

A photometer for carrying out such absorption measurements is known from U.S. Pat. No. 6,628,382 B2. A drop of liquid is held between two faces, which are drawn close to each other, of two components based on its surface tension, and light is passed through this drop by means of optical fibres contained in the two components. A path length which is as large as possible, for achieving a measured signal which is as large as possible during the irradiation, is achieved as a result of the fact that the drop is stretched when the two components are moved apart from each other. This device is applied for carrying out individual measurements on a small number of samples; nevertheless, it would appear unsuitable for carrying out tests on a large number of samples in an automated manner. The evaporation rate in devices of this type, in which an individual liquid volume having a high height (path length) but very low diameter is examined, is very high.

These two devices for providing virtual wells, which are known in the art, are on the one hand very complex to produce and on the other hand are of only limited suitability or no suitability at all for examining a large number of liquid samples in an automated manner.

The object of the present invention is to propose an alternative device and/or an alternative method which eliminate or at least minimise the drawbacks known in the art.

According to a first aspect, the object is achieved by the features of independent claim 1, by proposing a micro cuvette assembly comprising a first partial plate with one or more first cuvette surfaces and a second partial plate which can be arranged relative to the first partial plate and has at least one or more second cuvette surfaces. These second cuvette surfaces are, in an active position of the micro cuvette assembly, arranged in register plane-parallel to the first cuvette surfaces and spaced apart therefrom by a distance. This forms, in the active position of the micro cuvette assembly, one or more micro cuvettes in which a liquid volume, applied previously to one of the cuvette surfaces, is held between these two cuvette surfaces. The micro cuvette assembly according to the invention is characterised in that each of the first cuvette surfaces of the first partial plate is formed individually and completely in each case by a surface of a transparent body which is accomplished as a free beam optical element and arranged in each case in an opening penetrating the first partial plate.

According to a second aspect, the object is achieved by the features of independent claim 19, by proposing a corresponding method for examining biological samples using a micro cuvette assembly of this type. In this case, at least one liquid volume to be examined is applied to one of the cuvette surfaces and the other cuvette surface is brought into contact with this liquid volume. Afterwards, both cuvette surfaces are brought in register into a plane-parallel position and at a distance from each other such that, in this active position of the micro cuvette assembly, there is formed at least one micro cuvette in which the liquid volume is held between these two cuvette surfaces. The method according to the invention is characterised in that each one of the first cuvette surfaces of the first partial plate is formed individually and completely in each case by a surface of a transparent body which is configured as a free beam optical element and arranged in one opening penetrating the first partial plate, wherein in each case at least one of these transparent bodies and the liquid volume, that is located between the two cuvette surfaces which are held at a fixed distance from each other, are penetrated by a light beam.

Additional preferred and inventive features result from the dependent claims.

Advantages of the micro cuvette assembly according to the invention include:

- One or a larger number of micro cuvettes are provided which all have a precisely defined height, so that the optical path length, which is precisely defined as a result, and the measurement of the optical density allow the determination of the concentration of a specific ingredient in a liquid sample manually and/or automatically in accordance with Lambert-Beer's Law.
- Absorption measurements can be carried out on very small volumes and at a defined path length.
- The micro cuvette assembly can have a footprint which is almost identical to a standard microplate. This turns it into an adapter allowing automatic absorption measurements to be carried out in micro cuvettes using a standard microplate reader.
- As a result of the irradiation of a large portion of the volume of a thin liquid sample with light, the absorption measurement is carried out at different points of the same sample. This greatly reduces any error-proneness of the measurement caused by inhomogeneous samples.

The large cuvette surfaces provided by the bodies of the micro cuvette assembly according to the invention minimise the influence of the evaporation of the liquid of an examined sample.

The micro cuvette assembly can have a footprint which is almost identical to a standard microplate. This turns it into an adapter allowing automatic absorption measurements to be carried out in micro cuvettes using a microplate reader.

Figure 1:
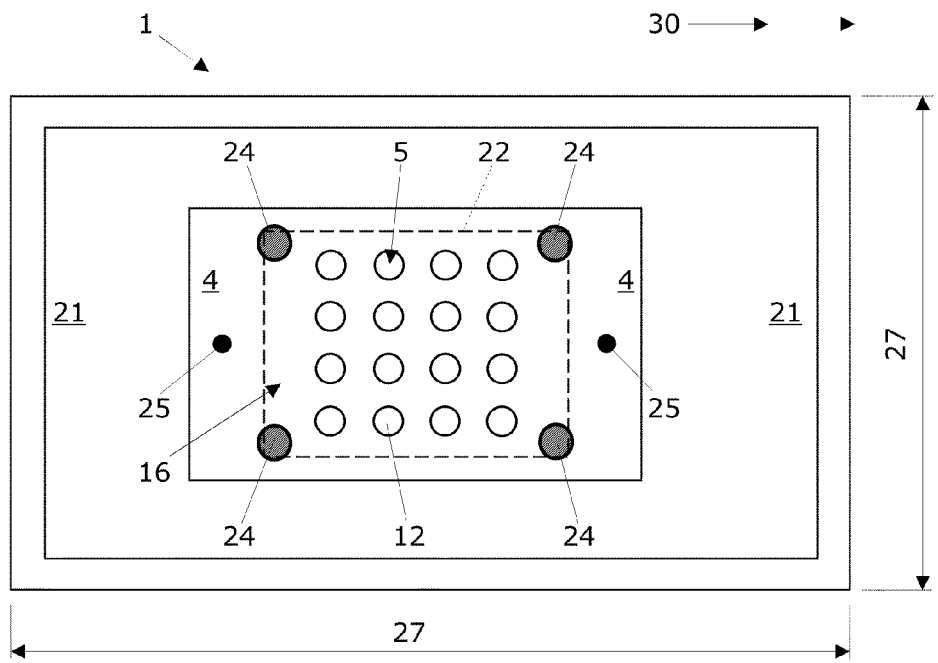
FIG. 1 is a plan view onto an open micro cuvette assembly according to a first or second embodiment.

FIG. 1 is a plan view onto an open micro cuvette assembly according to a first or second embodiment. The micro cuvette assembly 1 comprises a first partial plate 2 with one or more first cuvette surfaces 3 and a second partial plate 4 which can be arranged relative to the first partial plate and has at least one or more second cuvette surfaces 5. These second cuvette surfaces 5 are, in an active position of the micro cuvette assembly 1 (cf. FIG. 2), arranged in register plane-parallel to the first cuvette surfaces 3 and spaced apart therefrom by a distance 6. Thus, in the active position of the micro cuvette assembly 1, one or more micro cuvettes 7 are formed in which a respective liquid volume 8, applied previously to one of the cuvette surfaces 3,5, is held between these two cuvette surfaces 3,5. This holding of a liquid volume 8 between the two opposing cuvette surfaces 3,5 of the two partial plates 2,4 of the micro cuvette assembly 1 is based preferably on the surface tension of this liquid volume 8. Thereby, the two cuvette surfaces 3,5 are wetted by the liquid. Each of the first cuvette surfaces 3 of the first partial plate 2 is, according to the present invention, formed individually and completely in each case by a surface of a transparent body 10 which is accomplished as a free beam optical element and arranged in each case in an opening 9 penetrating the first partial plate 2 (cf. FIGS. 1-7).

In conjunction with the invention, it is hold that the numbering of these partial plates is arbitrary, and that the specific arrangements are mutually exchangeable and are claimed as correspondingly alternative embodiments. It is thus possible (as illustrated in FIG. 1) for the first partial plate 2 to be able to be arranged relative to the second partial plate 4. In fact, FIG. 1 shows only the second partial plate 4 in order to allow the plan view onto the cuvette surfaces 5 of the transparent bodies 10 which are accomplished as a free beam optical element. The transparent body 10 is preferably formed from a material which is selected from a group comprising glass, quartz glass, plastics material and ceramics, which is permeable to the electromagnetic waves used and has an index of refraction allowing the use as a free beam optical element.

As any person skilled in the art is aware, free beam optics (freistrahloptische Elemente) are based on the principle of the free propagation of light beams which are purposefully guided through lenses and other conventional optical elements. In contrast to free beam optics, fibre optics, such as are known for example from U.S. Pat. No. 6,628,382 B2, are based on the principle of total reflection inside an optical fiber. The use of free beam optical transparent bodies 10 allows the samples to be irradiated with an illumination having a large cross section; in addition, the divergence of the light beams as they leave the free beam optical, transparent bodies 10 is adjustable and in no way as great as in fibre optics.

The term "microplates" refers in conjunction with the present invention to all multiwell plates having a plurality of wells or vessels arranged in an array. Especially preferred microplates have at least approximately the dimensions and the footprint of a microplate in accordance with the SBS Standard, as published by the American National Standards Institute (ANSI). Although a large number of different shapes and dimensions of wells are known, a common feature of all standard microplates is nevertheless that they have a standardised footprint, and that the axial distance of the wells, which are each arranged in an array, is also standardised. This axial distance is, for example, in 24-well (4×6) plates 18 mm, in 96-well (8×12) plates 9 mm and in 384-well (16×24) plates 4.5 mm. All these standard microplates are consumable articles made of plastics material and are conventionally used just once and then disposed of.

Figure 2:
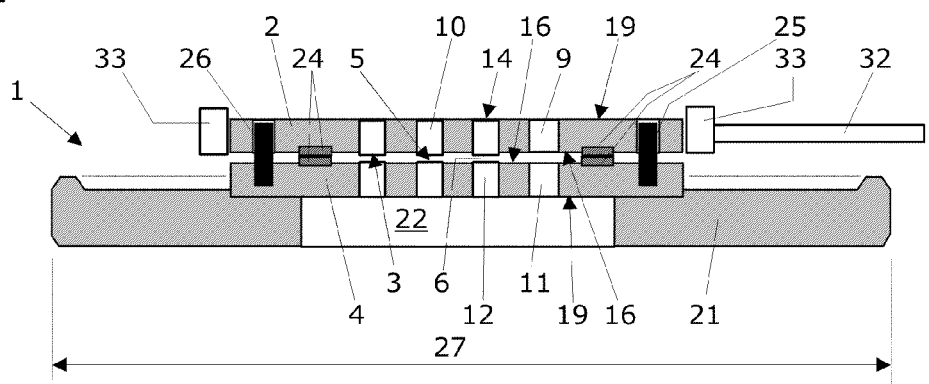
FIG. 2 is a vertical section through the micro cuvette assembly in FIG. 1, in the active position according to the first embodiment.

In the first embodiment, shown in FIG. 1, of the invention, each of the second cuvette surfaces 5 of the second partial plate 4 is formed individually and completely in each case by a surface of a transparent body 12 which is accomplished as a free beam optical element and arranged in each case in an opening 11 penetrating the second partial plate 4 (cf. also FIG. 2).

Preferably, all transparent bodies 10,12 are made of quartz glass, thus allowing light of a wavelength of from 200 to 1,000 nm to traverse (pass through) the transparent bodies 10,12. It is especially preferable that the transparent bodies 10,12 are accomplished substantially cylindrical; in this case, the cuvette surfaces 3 of the first partial plate 2 or the cuvette surfaces 3,5 of the first and second partial plates 2,4 consist of first circular surfaces of such cylinders (cf. also FIG. 5). Alternatively, the transparent bodies 10 can also be formed from a material which is selected from a group comprising glass, plastics material and ceramics, is permeable for the electromagnetic waves used and has an index of refraction allowing use as a free beam optical element.

The first and second embodiments of the micro cuvette assembly 1 according to the present invention each comprise a base plate 21 with a recess 22 (cf. FIGS. 2 and 3), the second partial plate 4 being accomplished to span this recess 22 and fixed to the base plate 21. The cuvette surfaces 3 of the second partial plate 4 are arranged in the region of this recess 22 (indicated by dashed lines in FIG. 1).

Preferably, the first and second partial plate 2,4 comprise spacers 24 which are accomplished to act on one another in such a way that, in the active position of the micro cuvette assembly 1, the fixed distance 6 between all opposing cuvette surfaces 3,5 of a micro cuvette assembly 1 is defined. For defining a sufficiently exact register position of the cuvette surfaces 3,5, the second partial plate 4 preferably comprises guide pins 25 which, in the active position of the micro cuvette assembly 1, are configured to dip into corresponding depressions 26 in the first partial plate 2.

In order to allow the automated use of the micro cuvette assembly 1 in a microplate reader, the micro cuvette assembly 1 according to the invention preferably has a footprint 27 almost identical to a standard microplate. At least, according to a first and second embodiment of the micro cuvette assembly 1 according to the present invention, the base plate 21 should have a footprint 27 corresponding at least approximately to the footprint of a standard microplate.

As may be seen from FIG. 1, the second partial plate 4 comprises a uniform arrangement of a plurality of cuvette surfaces 5. A 4×4 array is shown. Preferred however are regular arrangements of a plurality of cuvette surfaces 5 as a linear array with 8 or 12 cuvette surfaces 5. Especially preferred are in this case integral multiples of such linear arrays arranged parallel to one another, thus producing two or more parallel rows of 8 or 12 cuvette surfaces 5. Especially preferred are such arrays of cuvette surfaces 5 having a uniform axial distance corresponding to the axial distance of the wells of standard microplates (cf. FIG. 4).

FIG. 2 is a vertical section through the micro cuvette assembly in FIG. 1, in the active position according to the first embodiment. The first partial plate 2 of the micro cuvette assembly 1 with a plurality of first cuvette surfaces 3 is positioned on the second partial plate 4 having the same number of second cuvette surfaces 5. In this active position of the micro cuvette assembly 1, the two cuvette surfaces 3,5 of a micro cuvette 7 are arranged in register plane-parallel to each other and spaced apart from each other by a distance 6. A liquid volume 8, which was manually applied previously to one of the cuvette surfaces 5 by means of a pipette or using a liquid handling system, is held in this micro cuvette 7 between these two cuvette surfaces 3,5 (cf. FIGS. 1-7).

Figure 7:
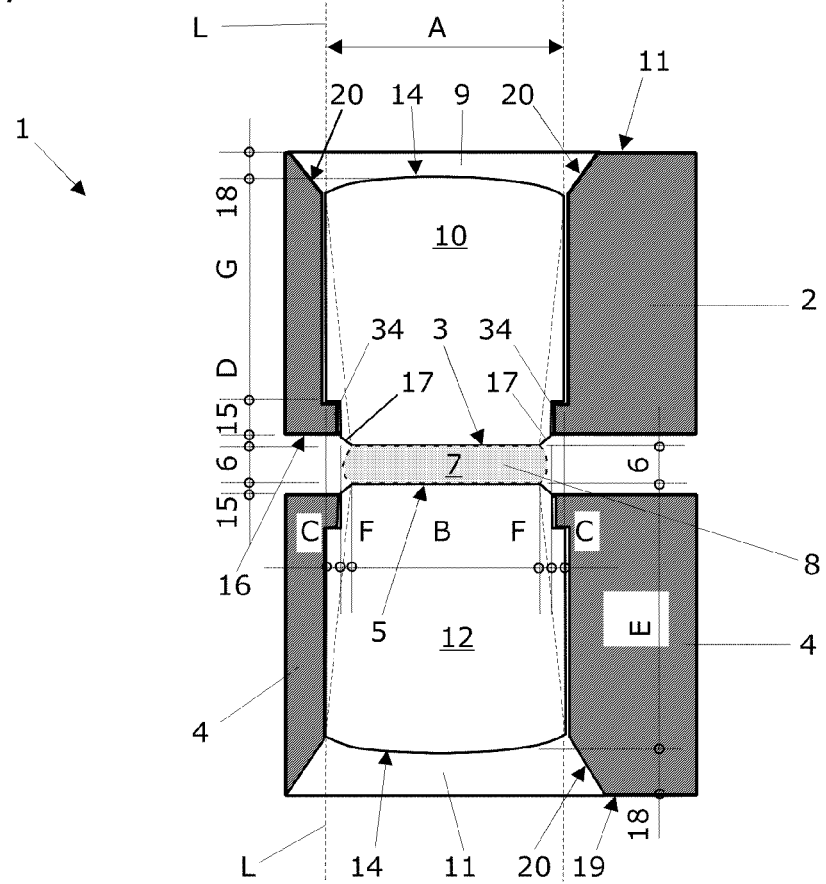
FIG. 7 is a vertical partial section through a closed and loaded micro cuvette of a micro cuvette assembly in the active position according to a preferred variant of the first and third embodiment.

The first embodiment of the micro cuvette assembly 1 is characterised in that each of the first cuvette surfaces 3 of the first partial plate 2 and the second cuvette surfaces 5 of the second partial plate 4 is formed individually and completely by a surface of a respective transparent body 10,12 which is accomplished as a free beam optical element and arranged in a respective opening 9,11 that penetrates the first partial plate 2 or the second partial plate 4. In FIG. 2, the transparent bodies 10,12 have been omitted in the opening 9, 11 arranged on the far right in the first and second partial plate 2,4, in order to show that these openings 9,11 completely penetrate the partial plates 2,4. FIG. 7 is an enlarged view of this cross section.

In addition, FIG. 2 shows how a robot gripper 33 of a robot 32 is used to position the first partial plate 2 on the second partial plate 4 and/or to raise the first partial plate 2 from the second partial plate 4. The first embodiment of the micro cuvette assembly 1 according to the invention comprises a base plate 21 with a footprint 27 corresponding at least approximately to the footprint of a standard microplate.

Figure 3:
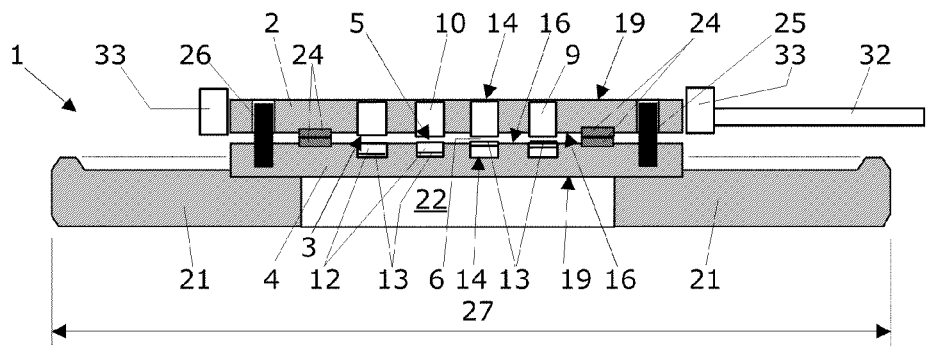
FIG. 3 is a vertical section through the micro cuvette assembly in FIG. 1, in the active position according to the second embodiment.

FIG. 3 is a vertical section through the micro cuvette assembly in FIG. 1, in the active position according to the second embodiment. As in the first embodiment, the first partial plate 2 of the micro cuvette assembly 1 with a plurality of first cuvette surfaces 3 lies on the second partial plate 4 with the same number of second cuvette surfaces 5. In this active position of the micro cuvette assembly 1 too, the two cuvette surfaces 3,5 of a micro-cuvette 7 are arranged in register plane-parallel to each other and spaced apart from each other by a distance 6. A liquid volume 8, which was manually applied previously to one of the cuvette surfaces 5 by means of a pipette or using a liquid handling system, is held in this micro-cuvette 7 between these two cuvette surfaces 3,5.

The second embodiment of the micro cuvette assembly 1 is characterised in that each of the first cuvette surfaces 3 of the first partial plate 2 is formed individually and completely in each case by a surface of a transparent body 10 which is accomplished as a free beam optical element and arranged in each case in an opening 9 penetrating the first partial plate 2, and in that each of the second cuvette surfaces 5 of the second partial plate 4 is formed individually and completely in each case by a surface of a mirror 13 arranged in each case in the second partial plate 4. Each of these mirrors 13 is provided with a reflective coating at the cuvette surface 5 or it comprises a transparent body 12 which is accomplished as a free beam optical element having a reflective-coated back side 14.

As stated hereinbefore, the first and second embodiments of the micro cuvette assembly 1 according to the present invention each comprise a base plate 21 with a recess 22 (cf. FIGS. 2 and 3), the second partial plate 4 being accomplished to span this recess 22 and fixed to the base plate 21. The cuvette surfaces 3 of the second partial plate 4 are arranged in the region of this recess 22 (indicated by broken lines in FIG. 1).

In the second embodiment too, it is preferred that all transparent bodies 10,12 are made of quartz glass, thus allowing the transparent bodies 10,12 to be penetrated with light of a wavelength of from 200 to 1,000 nm. Particularly preferably, the transparent bodies 10,12 are accomplished substantially cylindrical; in this case, the cuvette surfaces 3 of the first partial plate 2 or the cuvette surfaces 3,5 of the first and second partial plates 2,4 consist of first circular surfaces of such cylinders (cf. also FIG. 5). This also applies to mirrors 13, if comprising a transparent body 10 which is provided on its back with a reflective coating (cf. the left two mirrors 13 in FIG. 2). It is equally preferred that all mirrors 13 define, irrespective of whether they are provided with a reflective coating at their front side (cf. the right two mirrors 13 in FIG. 2) or back side, a circular cuvette surface 5.

The robot gripper 33, shown in FIG. 3, of a robot 32 can also be used to position the base plate 21 with the second partial plate 4 on the surface of a work space (for example on the surface of a microplate carrier of a workstation) and/or to raise the base plate 21 with the first and second partial plate 2,4 from the surface of a work space and transfer it to a microplate reader. This is possible also because the second embodiment of the micro cuvette assembly 1 according to the present invention comprises a base plate 21 with a footprint 27 corresponding at least approximately to the footprint of a standard microplate.

Figure 4:
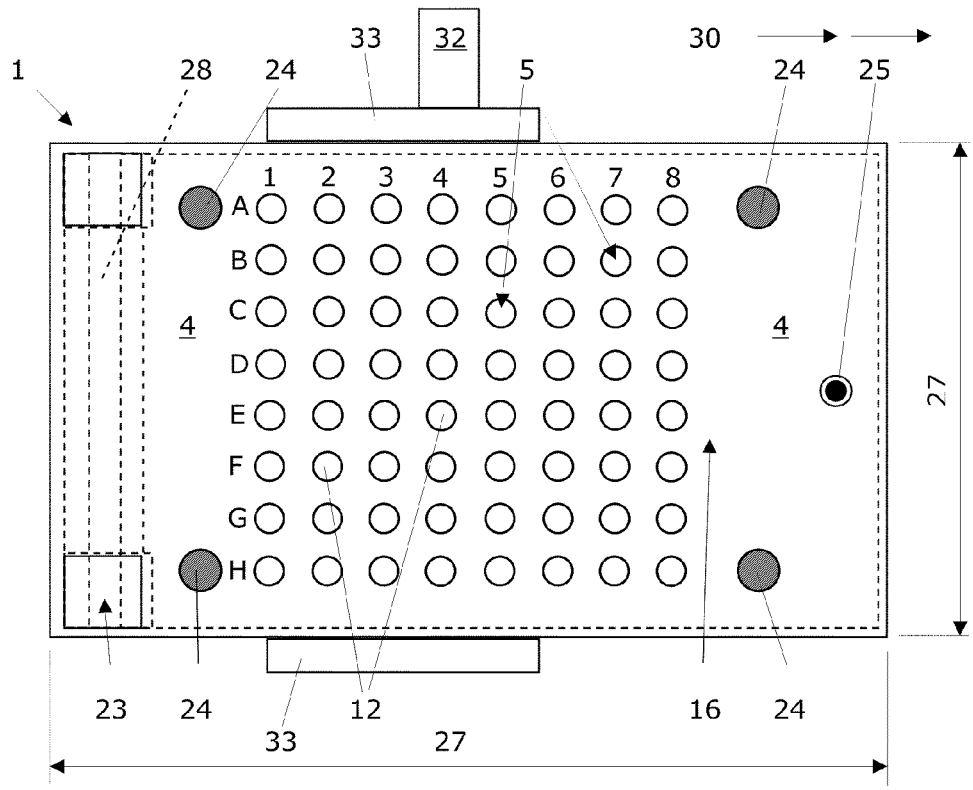
FIG. 4 is a plan view onto an open micro cuvette assembly according to a third embodiment.

FIG. 4 is a plan view onto an open micro cuvette assembly 1 according to a third embodiment. The second partial plate 4 of the micro cuvette assembly 1 comprises in this case 64 second cuvette surfaces 5. The first partial plate 2, which is arrangeable relative to this second partial plate 4, has been removed and is indicated here merely by dashed lines. Naturally, both partial plates 2,4 have the same number and distribution of first and second cuvette surfaces 3,5 which, in an active position of the micro cuvette assembly 1 (cf. FIG. 5), are arranged in register plane-parallel to one another and spaced from one another by a distance 6. This forms, in the active position of this micro cuvette assembly 1 illustrated here, 64 micro cuvettes 7, in each of which a liquid volume 8 applied previously to one of the cuvette surfaces 3,5 is held between these two cuvette surfaces 3,5.

The third embodiment of the micro cuvette assembly 1 is characterised in that each of the first cuvette surfaces 3 of the first partial plate 2 and the second cuvette surfaces 5 of the second partial plate 4 is formed individually and completely in each case by a surface of a transparent body 10,12 which is accomplished as a free beam optical element and arranged in a respective opening 9,11 that penetrates the first partial plate 2 or the second partial plate 4. The third embodiment of the micro cuvette assembly 1 according to the invention comprises a first partial plate 2 and a second partial plate 4 which are connected via a joint 23 which has an axis 28 and by means of which one of these partial plates 2,4 can be swivelled onto the other partial plate 4,2 for establishing the active position of the micro cuvette assembly 1.

Preferably, the first and second partial plate 2,4 comprises spacers 24 which are accomplished to act on one another in such a way that, in the active position of the micro cuvette assembly 1, the fixed distance 6 between all opposing cuvette surfaces 3,5 of a micro cuvette assembly 1 is defined. Preferably, the second partial plate 4 comprises guide pins 25 which, in the active position of the micro cuvette assembly 1, are accomplished to dip into corresponding depressions 26 in the first partial plate 2. Especially preferable, the second partial plate 4 has a footprint 27 corresponding at least approximately to the footprint of a standard microplate.

As may be seen from FIG. 4, the second partial plate 4 comprises a regular arrangement of a plurality of cuvette surfaces 5. An 8×8 array is shown. Preferred, on the other hand, are uniform arrangements of a plurality of cuvette surfaces 5 as a linear array with 8 or 12 cuvette surfaces 5. Especially preferred are in this case integral multiples of such linear arrays arranged parallel to one another, thus producing two or more parallel rows of 8 or 12 cuvette surfaces 5. Especially preferred are arrays of cuvette surfaces 5 having a uniform axial distance corresponding to the axial distance of the wells of standard microplates. In accordance with the designation of the wells of a standard microplate, the cuvette surfaces 5 on which the liquid volumes 8 are to be deposited can therefore, as shown, also be identified in columns 1-8 or 1-12 (not shown) and in rows A-H.

Figure 6:
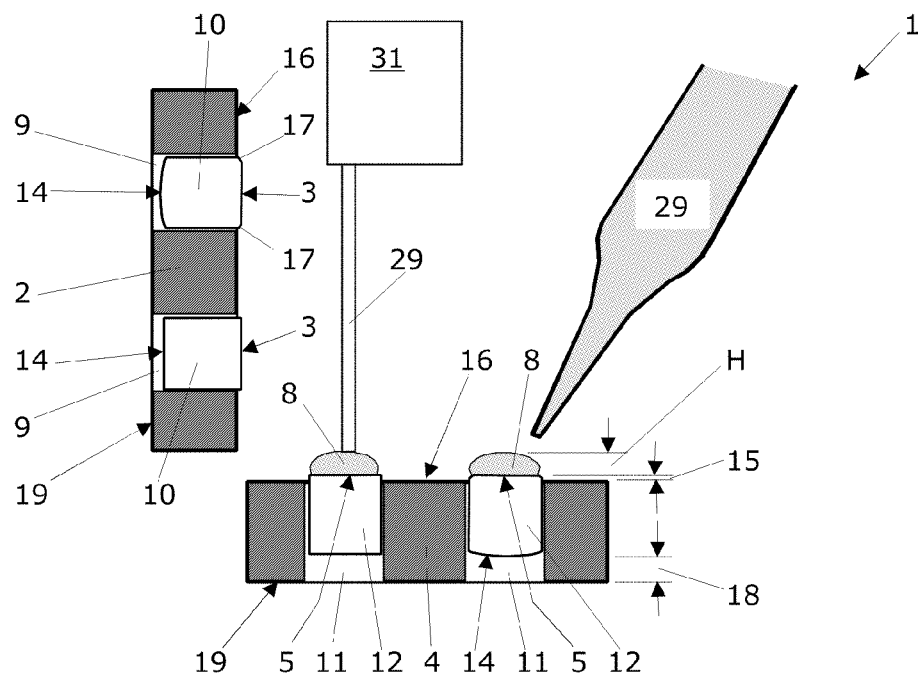
FIG. 6 is a vertical partial section through an open micro cuvette assembly according to a first and second variant of the first and third embodiment.

The robot gripper 33 of a robot 32, shown in FIG. 4, can also be used to position the micro cuvette assembly 1 on the surface of a work space (for example on the surface of a microplate carrier of a workstation), where the liquid volumes 8 can be dispensed onto the cuvette surfaces 5 by means of a liquid handling system 31 (cf. FIG. 6). In addition, such micro cuvette assemblies 1 with the robot gripper 33 of the robot 32 can be transferred to a microplate reader 30 (see the double-headed arrow), where absorption measurements can be carried out on the liquid volumes 8 held in the micro cuvettes 7. This is possible also because the third embodiment of the micro cuvette assembly 1 according to the present invention comprises a second partial plate 4 with a footprint 27 corresponding at least approximately to the footprint of a standard microplate. With the micro cuvette assembly 1 according to the invention, luminescence measurements and/or fluorescence measurements can also be carried out in very small liquid volumes 8 of typically from 1 µl to 10 µl, especially preferably of 2 µl.

Figure 5:
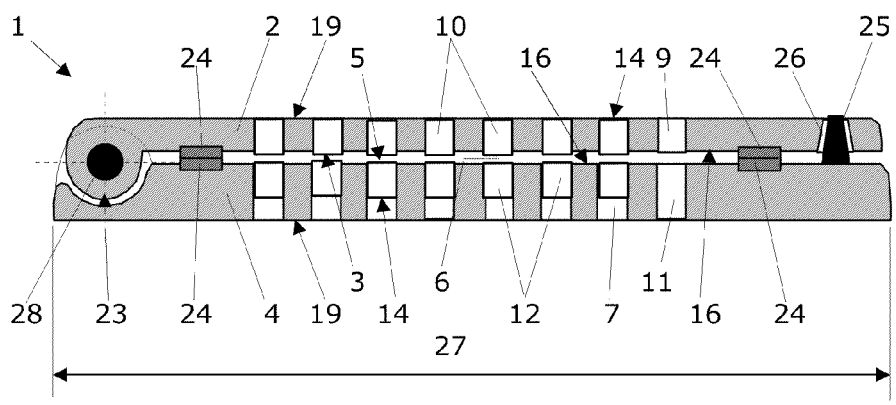
FIG. 5 is a vertical section through the micro cuvette assembly in FIG. 4, in the active position according to the third embodiment.

FIG. 5 is a vertical section through the micro cuvette assembly in FIG. 4, in the active position according to the third embodiment. In this case too, the transparent bodies 10,12 in the openings 9,11 arranged at the far right in the first and second partial plate 2,4 have been omitted in order to show that these openings 9,11 penetrate the partial plates 2,4 completely. FIG. 7 is an enlarged view of this cross section. The elements of the third embodiment shown here correspond substantially to the elements of the first embodiment (cf. FIG. 2) and have been described in greater detail hereinbefore.

Departing from the view in FIG. 5 and following FIG. 3, it is possible to conceive of a further variant of the micro cuvette assembly 1 according to the present invention (not shown), according to which each of the first cuvette surfaces 3 of the first partial plate 2 is formed individually and completely in each case by a surface of a transparent body 10 which is accomplished as a free beam optical element and arranged in each case in an opening 9 penetrating the first partial plate 2, wherein each of the second cuvette surfaces 5 of the second partial plate 4 being formed individually and completely in each case by a surface of a mirror 13 arranged in the second partial plate 4. Each of these mirrors 13 is provided with a reflective coating at the cuvette surface 5 or it comprises a transparent body 12 which is configured as a free beam optical element and has a reflective-coated back 14.

FIG. 6 is a vertical partial section through an open micro cuvette assembly according to a first and second variant of the first and third embodiment, as have been described hereinbefore. It will be demonstrated with reference to this figure that it is aimed for achieving a substantially symmetrical arrangement of the two transparent bodies 10,12 which are accomplished as a free beam optical element. In order to ensure that a micro cuvette 7 having a preferred height of 0.5 mm is effectively filled, both cuvette surfaces 3,5 of a micro cuvette 7 should be wetted almost completely when taking the active position of the two partial plates 2,4 of a micro cuvette assembly 1. The drop height H which a liquid volume 8 is to have after application to a cuvette surface 3,5 is therefore somewhat more than the 0.5 mm of the distance 6; a drop height H of approx. 0.6 mm is preferred. As indicated, the liquid volumes 8 can be applied to the cuvette surfaces 3,5 by means of a hand-held pipette or in an automated manner by means of a pipette 29 of a liquid handling system 31.

Also disclosed here are especially preferred embodiment details. These include the especially preferred condition that the cuvette surfaces 3,5 of the transparent bodies 10,12 and the mirror 13 protrude by an overhang dimension 15 beyond the first surfaces 16 of the partial plates 2,4, adjoining those optical elements. It has surprisingly been found that an overhang dimension 15 of a few hundredths of a millimeter, in particular of 0.05 mm, is sufficient to prevent a liquid volume 8 applied to a cuvette surface 3,5 from spontaneously leaving this cuvette surface 3,5 again. This observation applies especially if the transparent bodies 10,12 are made of quartz glass and if the first surfaces 16 of the partial plates 2,4 are made of anodised aluminium; the selection of a black matt anodised aluminium or a black matt anodised aluminium alloy is particularly preferred in this regard. This observation is all the more remarkable because it has been found that the anodised aluminium surface is more hydrophilic than the relatively hydrophobic, finely polished quartz surface of the transparent bodies 10,12. The arrangement of such an overhang dimension 15 also has the advantage that no particles can be broken off from the respective partial mirror 2,4 and transferred to the transparent bodies during the fine grinding and fine polishing of the cuvette surfaces 3,5 of the transparent bodies 10,12.

In order to be able to carry out the cleaning of the cuvette surfaces 3,5 of the transparent bodies 10,12 more easily, the cuvette surfaces 3,5 of the transparent bodies 10,12 and the mirror 13 preferably have a broken edge 17 which is accomplished as a peripheral bevel or rounding. It is thus possible to prevent, when wiping the cuvette surfaces 3,5, the formation of lints at a sharp edge, which then additionally have to be removed from the cuvette surfaces 3,5 again. Despite the breaking of the edge 17, liquid volumes 8 applied to a cuvette surface 3,5 remain on this cuvette surface 3,5. Preferably, the overhang dimension 15 is 0.05 mm and the edge break is preferably accomplished as a 45° bevel over the entire overhang dimension.

In order to prevent traces of grease from fingerprints or else scratches from being able to form on the back sides 14 of the transparent bodies 10,12 when operating the micro cuvette assembly 1 according to the present invention, these transparent bodies 10,12 are preferably mounted in the partial plates 2,4 in such a way that their back sides 14 is offset from a second surface 19 of one of the two partial plates 2,4 by a set-back dimension 18. This set-back dimension 18 is preferably about 1.1 mm.

FIG. 7 is a vertical partial section through a closed and loaded micro cuvette of a micro cuvette assembly 1 in the active position according to a preferred variant of the first and third embodiment. The micro cuvette assembly 1 shown here comprises a first partial plate 2 with a first cuvette surface 3 and a second partial plate 4 which can be arranged relative to the first partial plate and has a second cuvette surface 5 which, in an active position of the micro cuvette assembly 1, is arranged in register plane-parallel to the first cuvette surface 3 and spaced apart by a distance 6, thus forming in the active position of the micro cuvette assembly 1 a micro cuvette 7 in which a liquid volume 8 applied previously to the cuvette surface 5 is held between these two cuvette surfaces 3,5. The liquid volumes 8 of the micro cuvette assembly 1 according to the present invention are typically from 1 µl to 10 µl, liquid volumes 8 of 2 µl being especially preferred.

The first cuvette surface 3 of the first partial plate 2 is formed individually and completely in each case by a surface of a transparent body 10 which is accomplished as a free beam optical element and arranged in each case in an opening 9 penetrating the first partial plate 2. Likewise, in this symmetrical arrangement, the second cuvette surface 5 of the second partial plate 4 is formed individually and completely by a surface of a transparent body 12 which is accomplished as a free beam optical element and arranged in an opening 11 penetrating the second partial plate 4.

Both transparent bodies 10,12 are made of quartz glass (preferably SQ2 from SCHOTT AG, D-55122 Mainz, Germany) and are accomplished substantially cylindrical, the cuvette surface 3 of the first partial plate 2 and the cuvette surface 5 of the second partial plate 4 consisting of first circular surfaces of these cylinders. The partial plates are made of anodised aluminium or an anodised aluminium alloy, preferably of black matt anodised AlMg4,5Mn.

The cuvette surfaces 3,5 of the transparent bodies 10,12 preferably protrude by an overhang dimension 15 of 0.05 mm beyond the first surfaces 16 of the partial plates 2,4 adjoining these optical elements, and have a broken edge 17 which is accomplished as a peripheral 45o bevel. These transparent bodies 10,12 are mounted in the partial plates 2,4 in such a way that their back side 14 is offset from a second surface 19 of one of the two partial plates 2,4 by a set-back dimension 18 of 1.1 mm. The transparent bodies 10,12 comprise a back side 14 which is lenticular, as a result of which light L beaming onto the back side 14 of the transparent bodies 10,12 is concentrated on its cuvette surfaces 3,5. Thus, both transparent bodies have identical free beam optical features, such as for example an inlet opening A (having a preferred diameter of 2.5 mm) for light being incident into the transparent body 10,12 and an outlet opening B (having a preferred diameter of 2.0 mm) for light coming from the transparent body 10,12, and being incident on the micro cuvette 7, the outlet opening corresponding precisely to the cuvette surface 3,5.

In FIG. 7, the reference numerals correspond to especially preferred dimensions of the transparent bodies 10, 12 according to the present invention, C corresponding to the projection or the dimension of 0.15 mm of a collar 34 which is formed in the partial plates 2,4 and which serves to position the transparent bodies 10,12 in the openings 9,11 the partial plates 2,4. The collar depth D is in this case 0.5 mm. The height E of the transparent bodies is approx. 4 mm. The 45o bevel measures 0.05 mm. The cylindrical part of the transparent body is 3.0 mm high. The distance 6 measures in this case 0.5 mm with a maximum tolerance of +/−5/1,000 mm. The openings 9,11, which penetrate the first or the second partial plate 2,4, each comprise a cone 20 which adjoins the back side 10 of the transparent bodies 10,12.

The above-described micro cuvette assembly 1 according to the present invention is ideal for carrying out a method for examining biological samples. In this method, at least one liquid volume 8 to be examined is applied to one of the cuvette surfaces 3,5 and the other cuvette surface 5,3 is brought into contact with this liquid volume 8. Afterwards, both cuvette surfaces 3,5 are brought in register into a plane-parallel position and at a distance 6 from each other such that there is formed, in this active position of the micro cuvette assembly 1, at least one micro cuvette 7 in which the liquid volume 8 is held between these two cuvette surfaces 3,5.

The method according to the present invention is characterised in that each of the first cuvette surfaces 3 of the first partial plate 2 is formed individually and completely in each case by a surface of a respective transparent body 10 which is accomplished as a free beam optical element and arranged in each case in an respective opening 9 penetrating the first partial plate 2, light passing in each case through one of these transparent bodies 10 and the liquid volume 8 located between the two cuvette surfaces 3,5 which are held at a fixed distance 6 from each other.

If each of the second cuvette surfaces 5 of the second partial plate 4 is formed individually and completely in each case by a surface of a transparent body 12 which is accomplished as a free beam optical element and arranged in each case in an opening 11 penetrating the second partial plate 4, light passes in one direction through both transparent bodies 10,12 and the liquid volume 8 located between the two cuvette surfaces 3,5, which are held at a fixed distance 6 from each other, of a micro cuvette assembly 1. In this specific method corresponding to a first embodiment, the path length of the light in the liquid volume 8 to be examined is thus 0.5 mm.

If each of the second cuvette surfaces 5 of the second partial plate 4 is formed individually and completely in each case by a surface of a mirror 13 arranged in the second partial plate 4, light passes in two directions through at least one transparent body 10 and the liquid volume 8 located between the two cuvette surfaces 3,5, which are held at a fixed distance 6 from each other, of a micro cuvette assembly 1. This specific method corresponding to a second embodiment thus doubles the length of the path of the light in the liquid volume 8 to be examined to a total of 1.0 mm. This leads to an improved signal-to-noise ratio when carrying out absorption measurements, in particular in samples having low absorption.

Both embodiments of the method according to the present invention using the micro cuvette assembly 1 according to the present invention allow different embodiment variants.

Thus it may be provided for that in a liquid volume 8 located between the two cuvette surfaces 3,5, which are held at a fixed distance 6 from each other in the micro cuvette assembly 1, one or two measurements may be carried out, using light of one or two wavelengths lying within one or two absorption bands of a sample to be examined. Especially preferred are in this case absorption measurements with light of a wavelength in the range of 260 nm (the absorption band of nucleic acids) and/or with light of a wavelength in the range of 280 nm (the absorption band of proteins).

If a respective measurement is carried out in a liquid volume 8 with light of a wavelength in the range of 260 nm and in the range of 280 nm, the ratio of the two absorption values for this liquid volume 8 can be determined and taken as a measure of the purity of the nucleic acid present in the liquid volume 8.

In addition to the above-mentioned single or double absorption measurements, reference measurements are preferably carried out with light of a wavelength lying outside one absorption band or outside two absorption bands of a sample to be examined, for example with light in the near UV range having wavelengths of between 300 and 400 nm. Depending on the microplate reader used, wavelengths in the range of for example 310 or 315 nm are especially preferred for reference measurements of this type—corresponding to the current apparatus properties. Reference measurements with light having a wavelength of from 400 to 1,000 nm are also preferred.

Because the second partial plate 4 of the micro cuvette assembly 1 or a base plate 21 on a second partial plate 4 of the micro cuvette assembly 1 preferably comprises a footprint 27 corresponding at least approximately to the footprint of a standard microplate, light of a microplate reader 30 can traverse the liquid volumes 8 located between two cuvette surfaces 3,5 of a micro cuvette assembly 1, which are held at a fixed distance 6 from each other.

As is generally known, the concentration of a substance dissolved in a liquid volume and the optical absorption of this liquid volume are linked to each other by the Lambert-Beer's Law ($A = c * \epsilon * l$),
wherein:
A=optical absorption
c=concentration of the dissolved substance [M=mol/L]
$\epsilon$=molar extinction coefficient of the dissolved substance [1/(M*cm)]
l=layer thickness of the liquid or length of the path length which the light has to pass through)[cm].

As a result of the precise definition of the path length, i.e. of the distance 6 between the two cuvette surfaces 3,5 of one or a number of micro cuvettes 7 of a micro cuvette assembly 1 according to the present invention, highly reproducible results are attained.

The same features or elements of the micro cuvette assembly 1 according to the present invention are provided in each case with the same reference numerals, even if these elements are not described in detail in all cases. Combinations of the embodiments illustrated or described form part of the scope of the present invention.

All described absorption measurements in a microplate reader and all described transportations with a robot can be carried out in an automated manner.

LIST OF REFERENCE NUMERALS

| | |
|---|---|
| 1 | Micro cuvette assembly |
| 2 | First partial plate |
| 3 | First cuvette surfaces |
| 4 | Second partial plate |
| 5 | Second cuvette surfaces |
| 6 | Distance |
| 7 | Micro cuvette |
| 8 | Liquid volume |
| 9 | Opening in 2 |
| 10 | Transparent body in 2 |
| 11 | Opening in 4 |
| 12 | Transparent body in 4 |
| 13 | Mirror |
| 14 | Back side of the transparent body |
| 15 | Overhang dimension |
| 16 | First surfaces of 2, 4 |
| 17 | Broken edge |
| 18 | Set-back dimension |
| 19 | Second surfaces of 2, 4 |
| 20 | Cone |
| 21 | Base plate |
| 22 | Recess |
| 23 | Joint |
| 24 | Spacer |
| 25 | Guide pins |
| 26 | Depressions |
| 27 | Footprint |
| 28 | Axis |
| 29 | Pipette |
| 30 | Microplate reader |
| 31 | Liquid handling system |
| 32 | Robot |
| 33 | Robot gripper |
| 34 | Collar |
| A | Inlet opening |
| B | Outlet opening |
| C | Collar dimension |
| D | Collar depth |
| E | Height of the transparent body |
| F | Bevel |
| G | Cylinder |
| H | Drop height |
| L | Light |

The invention claimed is:

1. A micro cuvette assembly (1) for examining biological samples, comprising a first partial plate (2) with one or more plane first cuvette surfaces (3) and a second partial plate (4) which is configured to be arranged relative to the first partial plate (2) and has at least one or more plane second cuvette surfaces (5) which, in an active position of the micro cuvette assembly (1), are arranged in register plane-parallel to the first cuvette surfaces (3) and spaced apart therefrom by a distance (6), thus forming in the active position of the micro cuvette assembly (1) one or more micro cuvettes (7) in which a liquid volume (8) applied previously to one of the cuvette surfaces (3,5) is held between these two cuvette surfaces (3,5) such that the two cuvette surfaces (3,5) are wetted by the liquid volume (8),
wherein each of the first cuvette surfaces (3) of the first partial plate (2) is formed individually and completely in each case by a surface of a transparent body (10) which is of a different material than the first partial plate (2) and which is configured as a free beam optical element and arranged in each case in an opening (9) that completely penetrates the first partial plate (2);
wherein the cuvette surfaces (3) of the transparent bodies (10) protrude by an overhang dimension (15) beyond first surfaces (16) of the first partial plate (2) that adjoin said cuvette surfaces (3); and
wherein the transparent bodies (10) are mounted in the first partial plate (2) in such a way that a back side (14) of the transparent bodies (10) is located inside of the first partial plate (2) and offset from a second surface (19) of the first partial plate (2) by a set-back dimension (18).

2. The micro cuvette assembly (1) according to claim 1, wherein the transparent bodies (10,12) are formed from a material selected from a group comprising glass, quartz glass, plastics material and ceramics.

3. The micro cuvette assembly (1) according to claim 1, wherein all transparent bodies (10,12) are made of quartz glass.

4. The micro cuvette assembly (1) according to claim 1, wherein the transparent bodies (10,12) are configured substantially cylindrical, and wherein the cuvette surfaces (3) of the first partial plates 2 or the cuvette surfaces (3, 5) of the first and second partial plates (2,4) consist of first circular surfaces of such cylinders.

5. The micro cuvette assembly (1) according to claim 1, wherein the micro cuvette assembly (1) comprises a base plate (21) with a recess (22), wherein the second partial plate (4) is configured to span this recess (22) and to be fixed to the base plate (21), and the cuvette surfaces (3) of the second partial plate (4) being arranged in the region of this recess (22).

6. The micro cuvette assembly (1) according to claim 5, wherein the base plate (21) has a footprint (27) corresponding at least approximately to a footprint of a standard microplate in accordance with the SBS Standard, as published by the American National Standards Institute (ANSI).

7. The micro cuvette assembly (1) according to claim 1, wherein the first partial plate (2) and the second partial plate (4) are connected by a joint (23) by means of which one of these partial plates (2,4) can be swivelled onto the other partial plate (4,2) for establishing the active position of the micro cuvette assembly (1).

8. The micro cuvette assembly (1) according to claim 7, wherein the first and second partial plate (2,4) comprise spacers (24) which are configured to act on one another in such a way that, in the active position of the micro cuvette assembly (1), the fixed distance (6) between all the opposing cuvette surfaces (3,5) of a micro cuvette assembly (1) is defined.

9. The micro cuvette assembly (1) according to claim 7, wherein the second partial plate (4) comprises guide pins (25) which, in the active position of the micro cuvette assembly (1), are configured to dip into corresponding depressions (26) in the first partial plate (2).

10. The micro cuvette assembly (1) according to claim 7, wherein the second partial plate (4) has a footprint (27) corresponding at least approximately to the footprint of a standard microplate in accordance with the SBS Standard, as published by the American National Standards Institute (ANSI).

11. The micro cuvette assembly (1) according to claim 1, wherein the first partial plate (2) and the second partial plate (4) each comprise a uniform arrangement of a plurality of cuvette surfaces (3,5).

12. The micro cuvette assembly (1) according to claim 11, wherein said uniform arrangements of a plurality of cuvette surfaces (3,5) are configured as a linear array with 8 or 12 cuvette surfaces (3,5) or as an integral multiple of such linear arrays arranged parallel to one another.

13. The micro cuvette assembly (1) according to claim 1, wherein each of the second cuvette surfaces (5) of the second partial plate (4) is formed individually and completely in each case by a surface of a transparent body (12) which is of a different material than the second partial plate (4) and which is configured as a free beam optical element and arranged in each case in an opening (11) that completely penetrates the second partial plate (4);
wherein the cuvette surfaces (5) of the transparent bodies (12) protrude by an overhang dimension (15) beyond first surfaces (16) of the second partial plate (4) that adjoin said cuvette surfaces (5); and
wherein the transparent bodies (12) are mounted in the second partial plate (4) in such a way that a back side (14) of the transparent bodies (12) is located inside of the second partial plate (4) and offset from a second surface (19) of the second partial plate (4) by a set-back dimension (18).

14. The micro cuvette assembly (1) according to claim 13, wherein the cuvette surfaces (3,5) of the transparent bodies (10,12) have a broken edge (17) which is configured as a peripheral bevel or rounding.

15. The micro cuvette assembly (1) according to claim 13, wherein the transparent bodies (10,12) comprise a back side (14) which is lenticular, as a result of which light being incident on the back side (14) of the transparent bodies (10, 12) is concentrated on its cuvette surface (3,5).

16. The micro cuvette assembly (1) according to claim 1,
wherein each of the second cuvette surfaces (5) of the second partial plate (4) is formed individually and completely in each case by a surface of a mirror (13) arranged in the second partial plate (4); and
wherein the cuvette surfaces (5) of the mirrors (13) protrude by an overhang dimension (15) beyond first surfaces (16) of the second partial plate (4) that adjoin said cuvette surfaces (5).

17. The micro cuvette assembly (1) according to claim 16, wherein each mirror (13) is provided with a reflective coating at the cuvette surface (5) or comprises a transparent body (12) which is configured as a free beam optical element and has a reflective-coated back side (14).

18. The micro cuvette assembly (1) according to claim 16, wherein the cuvette surfaces (5) of the mirror (13) have a broken edge (17) which is configured as a peripheral bevel or rounding.

19. The micro cuvette assembly (1) according to claim 1,
wherein in said distance (6) that spaces apart the first and second cuvette surfaces (3,5) from each other, the micro cuvettes (7) are void of surfaces which contact the liquid volume (8) that is held between said first and second cuvette surfaces (3,5).

20. The micro cuvette assembly (1) according to claim 1, wherein the first and second cuvette surfaces (3,5) are the only surfaces of the micro cuvette assembly (1) that are configured to contact the liquid volume (8) that is held between said first and second cuvette surfaces (3,5).

* * * * *